United States Patent [19]

Strid

[11] Patent Number: 5,386,012

[45] Date of Patent: Jan. 31, 1995

[54] GROWTH FACTOR IN CONNECTION WITH ARTIFICIAL IMPLANTS

[76] Inventor: Lars Strid, Raketgatan 5, S-413 20 Göteborg, Sweden

[21] Appl. No.: 180,497

[22] Filed: Jan. 12, 1994

Related U.S. Application Data

[63] Continuation of Ser. No. 916,126, Jul. 30, 1992, abandoned.

[30] Foreign Application Priority Data

Feb. 6, 1990 [SE] Sweden ................... 9000409

[51] Int. Cl.⁶ .................. A61K 37/02; A61L 27/00
[52] U.S. Cl. .................. 530/331; 530/345; 525/54.1
[58] Field of Search ............ 530/331, 345; 525/54.1

[56] References Cited

U.S. PATENT DOCUMENTS

| | | | |
|---|---|---|---|
| 4,584,284 | 4/1986 | Audhya et al. | 514/18 |
| 4,665,054 | 5/1987 | Pickart | 514/18 |
| 4,767,753 | 8/1988 | Pickart | 514/18 |
| 4,810,693 | 3/1989 | Pickart | 514/18 |
| 4,877,770 | 10/1989 | Pickart | 514/18 |
| 4,882,162 | 11/1989 | Ikada et al. | 514/18 |
| 5,059,588 | 10/1991 | Pickart | 514/12 |

FOREIGN PATENT DOCUMENTS

| | | |
|---|---|---|
| 0190736 | 8/1986 | European Pat. Off. |
| 0358819 | 3/1990 | European Pat. Off. |
| 8808714 | 11/1988 | WIPO |
| 8803417 | 5/1989 | WIPO |
| WO89/12441 | 12/1989 | WIPO |

*Primary Examiner*—Howard E. Schain
*Assistant Examiner*—Benet Prickril
*Attorney, Agent, or Firm*—Birch, Stewart, Kolasch & Birch

[57] ABSTRACT

This invention utilizes the biological activity of the copper complex of the tripeptide glycyl-L-histidyl-L-lysine. This peptide is covalently bound to artificial implants where it has a chemoattractive effect and also acts when it is released by hydrolysis of the implants. The peptide increases fibroblastic collagen synthesis thereby enabling a more rapid replacement of the implants with human tissue.

18 Claims, 2 Drawing Sheets

GROWTH FACTOR IN CONNECTION WITH ARTIFICIAL IMPLANTS

This application is a continuation of application Ser. No. 07/916,126 filed on Jul. 30, 1992, now abandoned.

TECHNICAL FIELD

This invention utilizes the biological activity of the copper complex of the tripeptide glycyl-L-histidyl-L-lysine. This peptide is covalently bound to artificial implants where it has a chemoattractive effect and also acts when it is released by hydrolysis of the implants. The peptide increases fibroblastic collagen synthesis thereby enabling a more rapid replacement of the implants with human tissue.

BACKGROUND

The evolution of multicellular organisms is dependent upon the ability of cells to communicate with each other and with their environment. One method the cells use for this communication is to release peptides that induce a specific activity in the receiving cell.

Such a peptide with biological activity is the human plasma growth factor copper-binding tripeptide glycyl-L-histidyl-L-lysine (GHK—$Cu^{2+}$).

L Pickart and S Lovejoy describe the properties of the peptide GHK—$Cu^{2+}$ in Methods in Enzymology, Vol 147 (1987) pp 314-328, Academic Press. It plays a physio-logical role in the healing of wounds by stimulation of the complex course of events necessary for the formation of new tissues such as angiogenesis and axon and dendrite growth in neurons. The peptide has also a chemoattractive effect on cells necessary for wound-healing such as macrophages, monocytes, mast cells and capillary endothelial cells.

Collagen is a fibrous protein that constitutes a quarter of the total amount of protein in the human body. It is the major fibrous element of skin, bone, tendons, cartilage, ligaments and blood vessels. Collagen is synthesized by fibroblasts, a type of cell localized in the area surrounding other cells and tissues.

In a publication in FEBS Letters 238 (1988) 343-346, F—X Maquart et al present data showing that GHK—$Cu^{2+}$ stimulates collagen synthesis in cultures of fibroblasts. This stimulation is observed at a peptide concentration as low as $10^{-12}M$ and reaches a maximum at $10^{-9}M$ where the increase in collagen synthesis is about 80%.

In European Patent Appliction 0190736, GHK—$Cu^{2+}$ with a modified C-terminal carboxyl group is used as an ointment for faster healing of wounds.

GHK—$Cu^{2+}$ possesses a significant superoxide dismutase-like activity with a rate constant of about 25% of the activity of enzymatic Cu,Zn-superoxide dismutase on a molar basis. When wounds and damaged tissue are present, cells from the immune system invade the injured area and large quantities of toxic oxygen radicals are released to kill invading bacteria. These radicals also destroy intact tissue which starts a vicious circle where more radicals are released, thus delaying healing. GHK—$Cu^{2+}$ superoxide dismutase activity detoxifies the tissue destroying superoxide anions.

Aggregation of blood platelets is the first stage of thrombosis. GHK—$Cu^{2+}$ inhibits this aggregation and it also inhibits the hormone thromboxane which causes thrombosis.

The structure of the tripeptide GHK—$Cu^{2+}$ is shown in FIG. 1. The affinity of the peptide for copper is very high with a pK for the dissociation constant of about 16. For biological activity the $\epsilon$-amino group on the side-chain of the lysine must be free.

THE TECHNICAL PROBLEM

Figure 1:
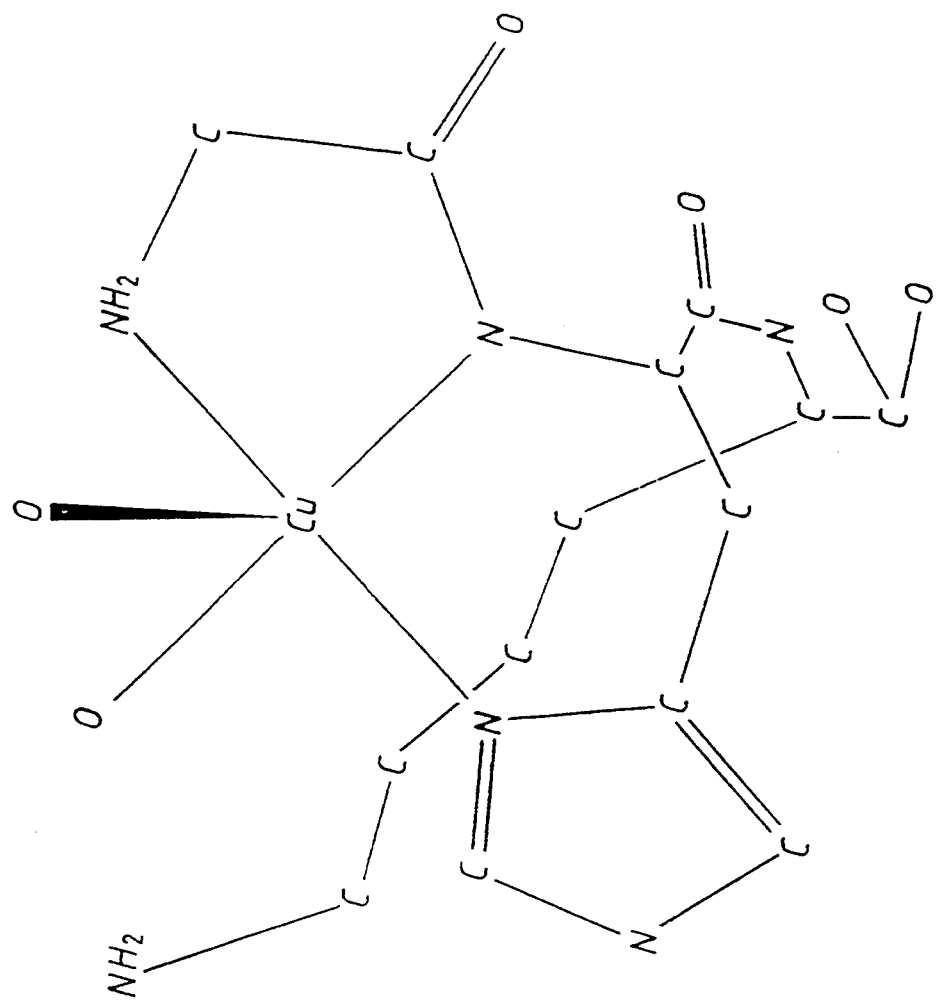
FIG. 1 illustrates the structure of the tripeptide GHK—$Cu^{+2}$ complex.

The use of artificial materials in surgery is gradually increasing. In orthopedic surgery, implants are used for soft parts such as muscles, tendons and ligaments. In the case of ligaments, the preferred material used has been polypropylene bands which are unfortunately not degradable, and results have been unfavorable in the long run. When degradable material is used to replace ligaments, it is of utmost importance that this material is biocompatible. Polymers of lactic acid and glycolic acid are degraded to nontoxic products that living tissues tolerate. In the human body they are hydrolysed to their monomers. Lactic acid is metabolized to carbon dioxide and water in the citric acid cycle while glycolic acid is excreted with the urine or is oxidized to pyruvate and is also metabolized in the citric acid cycle resulting in the same products as for lactic acid. These harmless products are very advantageous when compared with the hydrolysis products of many other polymers.

Polymers of lactic and glycolic acid have been used for long time as resorbable suture material. When this material is used for artificial ligaments the main problem is that they hydrolyse so rapidly that the body is not allowed enough time to replace them with its own tissue where collagen constitutes the main part. The rapid hydrolysis could be compensated for if one could increase the rate of collagen synthesis.

The solution:

The invention presented here is that the material used for implants incorporates GHK—$Cu^2$ the copper-complex of the tripeptide glycyl-L-histidyl-L-lysine. As may be seen in FIG. 1, the C-terminal carboxyl group is not involved in the binding of the tripeptide to copper, and for that reason the C-terminal carboxyl group is suitable for the covalent binding of the GHK—$Cu^{2+}$ peptide to implants.

With well-known peptide synthesis, the free carboxyl group of the peptide is coupled to a polymer containing free primary amino groups or to a polymer which can be modified to contain free amino groups. Since the peptide has maximal activity at a concentration as low as $10^{-9}M$ where it almost doubles the fibroblasts synthesis of collagen, it is fully sufficient that one peptide molecule is coupled to a polymer molecule having a molecular weight of 500,000.

Thought of chemoattraction and when the peptide GHK—$Cu^{2+}$ is released by hydrolysis of the implant in the tissues, very specific biological processes are started involving many closely coordinated reactions that must be in balance in order to allow healing to occur. This includes an increase in collagen synthesis, an increase of tissue-protective superoxide dismutase activity, and a chemoattractive effect on among others mast cells and capillary endothelial cells which accumulate at the transplant site, there stimulating new formation of blood vessels and the flow nourishment to the area.

Best mode of carrying out the invention:

EXAMPLE 1

The free carboxyl group of poly-L-lactic acid are activated with carbodiimide and then allowed to react with an excess of a diamine, $NH_2(CH_2)_nNH_2$ where $n==2-6$ depending upon the length of the desired spacer-arm. The carbodiimide will be dicyclohexylcarbodiimide if the reaction is carried out in organic solution, or 1-ethyl-3-(3-dimethylaminopropyl-)carbodiimide if the reaction is performed in a water solution.

The tripeptide $NH_2$-glycyl-L-histidyl-L-lysine-COOH is blocked on the amino group of glycine, the imidazole group of histidine and the $\epsilon$-amino group of lysine with 9-fluorenylmethyl chloroformate (FMOC-Cl). The free carboxyl group of lysine is activated with carboldiimide as described above and allowed to react with the free amino group of the derivative of poly-L-lactic acid [poly-L-lactic acid-C—NH(CH$_2$)$_n$—NH$_2$].

Figure 2:
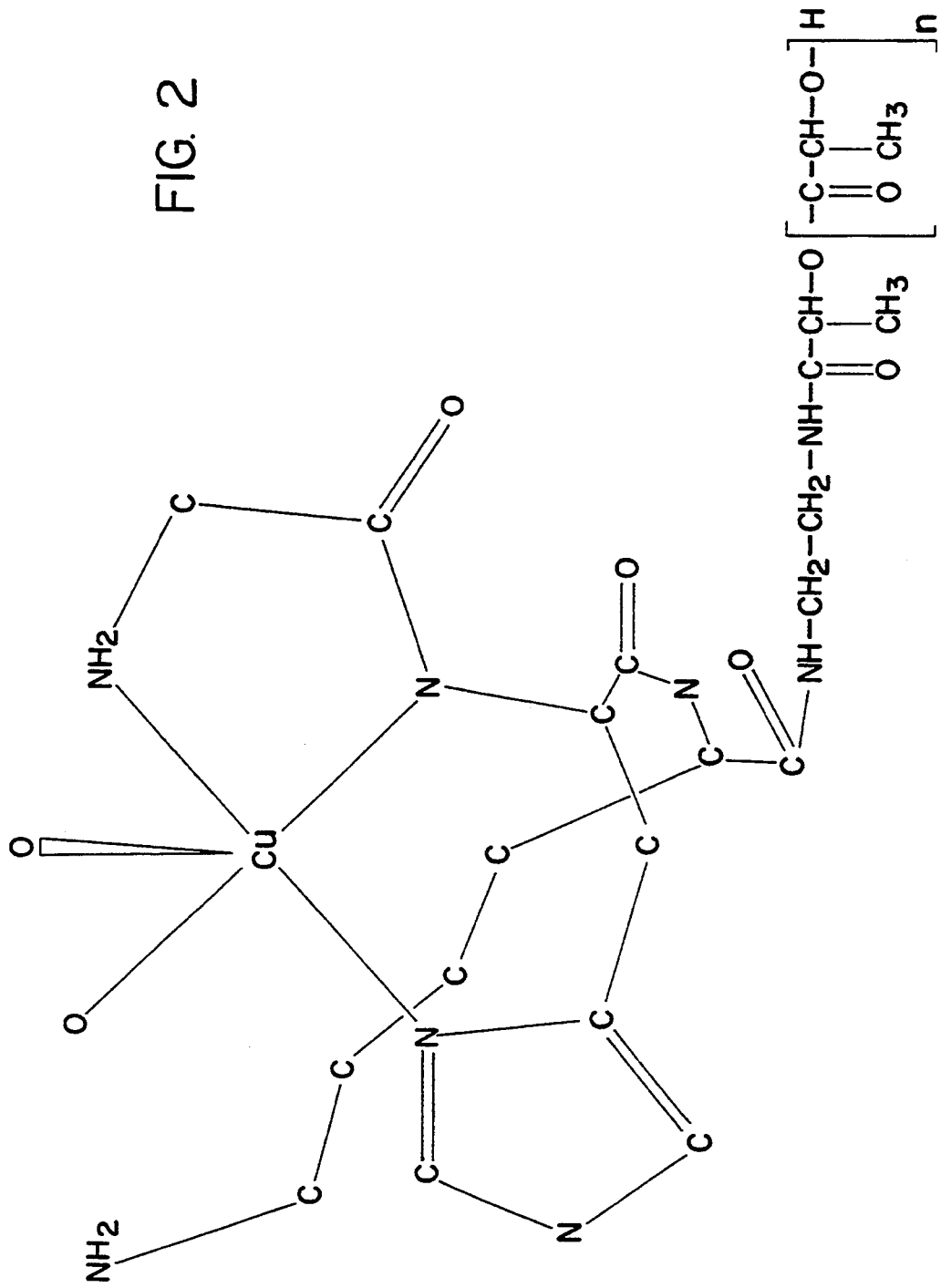
FIG. 2 illustrates the GHK—$Cu^{+2}$ complex covalently bound to polylactic acid via an ethylenediamine spacer.

After removal of the protective FMOC-groups with piperidine and the addition of copper (II) acetate the desired product is obtained, the structure of which is shown in FIG. 2. In this figure the diamine $NH_2(CH_2)_2NH_2$ has been used. The same methods of synthesis are also valid for poly-DL-lactic acid, poly-D-lactic acid, polyglycolic acid and their co-polymers.

Above, FMOC has been used as the blocking group. Another blocking agent is the tert-butoxycarbonyl group (t-BOC-). Deblocking after the synthesis is in this case performed with dilute acid (25% trifluoroacetic acid).

The peptide glycyl-L-histidyl-L-lysine is commercially available.
Other examples Another way for synthesis is by usual peptide synthesis coupling the amino blocked L-lysine, L-histidine and glycine one after the other to the amino derivative of the polymer.

Lactic acid and glycolic acid are α-hydroxycarboxylic acids. A number of other α-hydroxycarboxylic acids are useful for homo- or co-polymerization. Examples are α-hydroxybutyric acid, α-hydroxyisobutyric acid, α-hydroxyvaleric acid, α-hydroxyisovaleric acid. To increase the amount of peptides per polymer molecule, one can treat the poly-α-hydroxycarboxylic acid with mild hydrolysis to increase the available number of carboxyl groups. Among β-hydroxycarboxylic acid D-β-hydroxybutyric acid has been used as a polymer for implants (British Patent 1034123).

Polymer based on p-dioxanone has also been used as implants. This has the formula

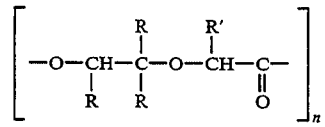

where R and R' represent hydrogen, methyl- or ethyl-groups and n the degree of polymerization.

Synthetic biodegradable polyester amides have been described by T H Barrows et al at 3M Center, St Paul, Minn., USA.

These polymers consist of units with the formula

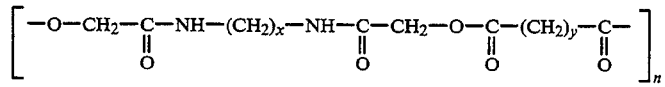

All of these polymers can be coupled covalently to GHK—$Cu^{2+}$ with the same methods described above.

Another method is to covalently couple GHK—$Cu^{2+}$ to other biocompatible materials, which may or may not be resorbed, that contain an amino group or a site where an amino group can be introduced. For example glass or silicic acid can be silylated with 3-aminopropyl-triethoxysilone. In this case a great number of GHK—$Cu^{2+}$ could be bound to the glass.

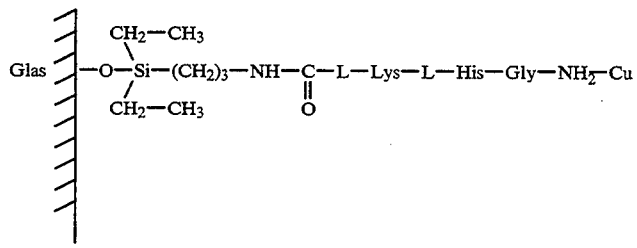

II

When metal implants are to be made the surface can first be covered with a protein, for instance serum albumin, and the amino groups bridge-bound with glutardialdehyde. After introduction of new amino groups the GHK—$CU^{2+}$ can be bound to the protein.

FIG. 1 shows the three-dimensional structure of GHK—$Cu^{2+}$. The side-chains of lysine and histidine and the amino terminal of glycine are necessary for the copper-binding and for the biological activity. One of the hydrogens of the α-carbon in the glycine can be exchanged with another radical without disturbing the conformation of the copper-complex. Proposals for new tripeprides can, for example, be Ala-His-Lys, Val-His-Lys or Leu-His-Lys. One advantage of this is that we can use the D-form of the amino-terminal amino acid which renders the peptide more resistant to proteolytic hydrolysis.

In the practical use of the invention reinforcing material can of course be used. This material can be degradable or not degradable.

Although the invention has been described here with reference to certain examples, it should be observed the invention is by no means restricted to such specific characteristics since closely related variations and modifications are obvious for the specialist in the field.

I claim:

1. An artificial implant material having the ability to increase natural collagen synthesis comprising a copper complex of the tripeptide glycyl-L-histidyl-L-lysine, which is bound to a biocompatible polymer through a covalent bond to the carboxyl group of the lysine.

2. The implant material of claim 1 wherein said copper complex is bound to said biocompatible polymer through a diamine compound.

3. The implant material of claim 2 wherein said polymer is formed from an α-hydroxycarboxylic acid.

4. The implant material of claim 3 wherein said polymer is formed from an α-hydroxycarboxylic acid selected form the group consisting of glycolic acid, lactic acid, butyric acid, isobutyric acid, valeric acid, isovaleric acid and mixtures thereof.

5. The implant material of claim 2 wherein a carboxyl group of said polymer forms a peptide bond with one amino-moiety of said diamine and the second amino-moiety of said diamine forms a peptide bond with the lysine moiety of said tripeptide-copper complex.

6. The implant material of claim 4 wherein said polymer is poly-L-lactic acid.

7. The implant material of claim 4 wherein said polymer is polyglycolic acid.

8. The implant material of claim 4 wherein said polymer is a copolymer of poly-L-lactic acid and polyglycolic acid.

9. The implant material of claim 5 wherein said implant material is poly-L-lactic acid.

10. The implant material of claim 5 wherein said implant material is polyglycolic acid.

11. The implant material of claim 5 wherein said implant material is a copolymer of poly-L-lactic acid and polyglycolic acid.

12. The implant material of claim 5 wherein said diamine is 1,6-hexanediamine.

13. The implant material of claim 2 wherein said biocompatible polymer is a polymer based on p-dioxanone having repeating units of the formula

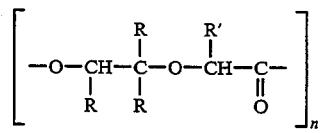

wherein R and R' are hydrogen, methyl or ethyl groups and n is a number between 15 and 700.

14. The implant material of claim 2 where said biocompatible polymer is a polymer based on p-dioxanone having repeating units of the formula

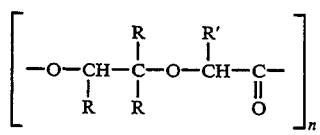

where R and R' are hydrogen, methyl or ethyl groups.

15. An artificial implant material having the ability to increase natural collagen synthesis comprising:
a) copper (II) complex of the tripeptide glycyl-L-histidyl-L-lysine; and
b) a biocompatible polymer selected from the group consisting of polymers of polylactic acid, polyglycolic acid, and copolymers thereof wherein said tripeptide is bound to said polymer through a diamine of the formula $NH_2-(CH_2)_n-NH_2$ wherein n is an integer from 2 to 6, and wherein one of the terminal amino groups of said diamine is bound to a free carbonyl group of said biocompatible polymer and the other terminal amino group of said diamine is bound to a free carbonyl group of the lysine of said copper (II) complex.

16. An artificial implants material according to claim 15, wherein said diamine is 1,6-hexanediamine.

17. An artificial implant material according to claim 16, wherein said biocompatible polymer is a polymer of poly-L-lactic acid.

18. An artificial implant material having the ability to increase natural collagen synthesis comprising a copper complex of the tripeptide glycyl-L-histidyl-L-lysine, wherein the C-terminal carboxyl group of said tripeptide is not involved in the copper complex and is covalently bound to a diamine compound through one amine moiety of said diamine, and the other amine moiety of said diamine is covalently bound to a biocompatible polymer.

* * * * *